(12) United States Patent
Ji et al.

(10) Patent No.: US 9,089,543 B2
(45) Date of Patent: Jul. 28, 2015

(54) ANTI-INFLAMMATORY COMPOSITION CONTAINING MACROLACTIN A AND A DERIVATIVE THEREOF AS ACTIVE INGREDIENTS

(75) Inventors: Young-Hoon Ji, Seoul (KR); Dong-Hee Kim, Gimhae-si (KR); Jae-Seon Kang, Busan (KR); Chun-Gyu Kim, Gimhae-si (KR); Sung-Uk Chung, Seoul (KR); Sung-Woo Hwang, Busan (KR); Kyung-Ran Kang, Busan (KR)

(73) Assignee: DAEWOO PHARMACEUTICAL IND. CO., LTD., Busan (KR)

( * ) Notice: Subject to any disclaimer, the term of this patent is extended or adjusted under 35 U.S.C. 154(b) by 461 days.

(21) Appl. No.: 13/321,112

(22) PCT Filed: May 24, 2010

(86) PCT No.: PCT/KR2010/003239
§ 371 (c)(1),
(2), (4) Date: Nov. 17, 2011

(87) PCT Pub. No.: WO2010/134790
PCT Pub. Date: Nov. 25, 2010

(65) Prior Publication Data
US 2012/0071549 A1  Mar. 22, 2012

(30) Foreign Application Priority Data

May 22, 2009 (KR) .......... 10-2009-0044900
Mar. 31, 2010 (KR) .......... 10-2010-0029016

(51) Int. Cl.
*A61K 31/335* (2006.01)
*A61K 31/365* (2006.01)

(52) U.S. Cl.
CPC ........... *A61K 31/335* (2013.01); *A61K 31/365* (2013.01)

(58) Field of Classification Search
CPC .................................................. A61K 31/365
USPC ........................................................ 514/450
See application file for complete search history.

(56) References Cited

U.S. PATENT DOCUMENTS 7,977,375 B2 * 7/2011 Timmis et al. ............. 514/450
2008/0039407 A1 * 2/2008 Timmis et al. ............. 514/31

FOREIGN PATENT DOCUMENTS

| EP | 1710248 | * 10/2006 |
| KR | 10-2006-0012393 A | 2/2006 |
| WO | 2006-032683 A1 | 3/2006 |
| WO | 2008-114954 A1 | 9/2008 |

OTHER PUBLICATIONS

Murphy "The role of bacteria in airway inflammation in exacerbations of chronic obstructive pulmonary disease," Curr. Opoin. Infect. Dis. 2006, vol. 19, pp. 225-230.*
Choi, et al., "Characteristics of the squalene synthase inhibitors produced by a Streptomyces species isolated from soils", Can. J. Microbiol., 2003, 49(11): 663-668.
Lee, et al., "Isolation and characterization of antimicrobial substance macrolactin A produced from Bacillus amyloliquefaciens CHO104 isolated from soil", Journal of Microbiology and Biotechnology, 2004, 14(3): 525-531.
Han, et al., "Biological control agent of common scab disease by antagonistic strain Bacillus sp. sunhua", Journal of Applied Microbiology, Apr. 11, 2005 (online), 99: 213-221.
Kim, et al., "Neuronal cell protection activity of macrolactin A produced by Actinomadura sp.", Journal of Microbiology and Biotechnology, 1997, 7(6): 429-434.
Nagano, et al., "Novel macrolactins as antibiotic lactones from a marine bacterium", J. Antibiot, 2001, 54(4): 333-339.
Magally, et al., "7-O-malonyl macrolactin A, a new macrolactin antibiotic from Bacillus subtilis active against methicillin-resistant staphylococcus aures, vancomycin-resistant enterococci, and a small-colony variant of Burkholderia cepacia", Antimicrobial Agents and Chemotherapy, 2006, 50(5): 1701-1709.
Gustafson, et al., "The macrolactins, a novel class of antiviral and cytotoxic macrolides from a deep-sea marine bacterium", J. Am. Chem. Soc., 1989, 111: 7519-7524.

* cited by examiner

*Primary Examiner* — Shengjun Wang
(74) *Attorney, Agent, or Firm* — Lucas & Mercanti, LLP

(57) ABSTRACT

The present invention relates to an anti-inflammatory use of macrolactin compounds such as macrolactin A, 7-O-malonyl macrolactin A and 7-O-succinyl macrolactin A, which are produced from a novel *Bacillus* strain of *Bacillus polyfermenticus* KJS-2 (KCCM10769P). The macrolactin compounds provided by the present invention were confirmed to greatly suppress the expression and formation of inducible nitric oxide synthetase (iNOS) and cyclooxygenase-2 (COX-2) which are proteins related to the formation of inflammatory mediators, and to accordingly inhibit the formation of nitric oxide (NO) and of prostaglandin E2 (PGE2) which are the metabolites of the proteins. In addition, the macrolactin compounds provided by the present invention were confirmed to have excellent effects in inhibiting the formation of tumor necrosis factor-alpha (TNF-α), interleukin-1β (IL-1β), interleukin-6 (IL-6) and granulocyte macrophage colony-stimulating factor (GM-CSF), which are pro-inflammatory cytokines. Therefore, the macrolactin compounds produced by the *Bacillus polyfermenticus* KJS-2 strain according to the present invention can provide excellent anti-inflammatory agents.

4 Claims, 9 Drawing Sheets

ANTI-INFLAMMATORY COMPOSITION CONTAINING MACROLACTIN A AND A DERIVATIVE THEREOF AS ACTIVE INGREDIENTS

CROSS-REFERENCE TO RELATED APPLICATIONS

This application is a 371 of PCT/KR2010/003239, filed on May 24, 2010, which claims the benefit of Korean Patent Application Nos. 10-2009-0044900, filed on May 22, 2009, and 10-2010-0029016, filed on Mar. 31, 2010, the contents of each of which are incorporated herein by reference.

TECHNICAL FIELD

The present invention relates to an anti-inflammatory use of macrolactin compounds such as macrolactin A (hereinafter, "MA"), 7-O-malonyl macrolactin A (hereinafter, "MMA"), and 7-O-succinyl macrolactin A (hereinafter, "SMA"), which are produced from *Bacillus polyfermenticus* KJS-2 (KCCM10769P). Concretely, the present invention relates to a use of the macrolactin compounds having a superior anti-inflammatory activity which is due to inhibition of the formation of inducible nitric oxide synthetase (hereinafter, "iNOS") and cyclooxygenase-2 (hereinafter, "COX-2"), and of tumor necrosis factor-alpha (hereinafter, "TNF-α"), interleukin-1β (hereinafter, "IL-1β"), interleukin-6 (hereinafter, "IL-6") and granulocyte macrophage colony-stimulating factor (hereinafter, "GM-CSF") which are pro-inflammatory cytokines.

BACKGROUND ART

Macrolactin compounds are macrolide antibiotics having a 24-membered lactone ring (J. Am. Chem. Soc., 1989, 111, 7519-7524). It has been reported that the compounds are produced from unclassified ocean bacteria, *actinomyces* and *Bacillus* strains, and 21 macrolactin compounds have been identified. These macrolactin compounds have a variety of pharmacological activities. Prior studies on the pharmacological activities of the macrolactin compounds are as follows.

William Fenical disclosed anti-viral activity of MA against Herpes simplex and HIV in 1989. Ick-Dong Yoo obtained MA from *Actinomadura* sp. strain in 1997 and studied protection of neurocytes derived from glutamate using the MA. In 2001, Hiroshi Sano isolated MA from *Bacillus* sp. PP19-H3 strain and studied the anti-bacterial activity of MA against *Staphylococcus aureus* IFO 12732 and *Bacillus subtilis* IFO 3134 strains. Sung-Won Choi obtained MA from *Streptomyces* sp. YB-401 strain in 2003 and disclosed the inhibition effect of MA on biosynthesis of cholesterol. In 2004, Keun-Hyung Park separated MA from *Bacillus amyloliquefaciens* CHO104 strain and studied anti-bacterial activity of MA against *Staphylococcus aureus* KCTC 1928, *Escherichia coli* KCTC 2593 and *Botrytis cinerea*. Joo-Won Suh obtained MA from *Bacillus* sp. Sunhua strain in 2005 and studied inhibition of the *Streptomyces* scabies inducing potato common scab using the MA. In 2006, Gabriella Molinari isolated MA, MMA and SMA from *Bacillus subtilis* DSM 16696 strain and studied anti-bacterial activity of each compound against vancomycin-resistant Enterococci (VRE), methicillin-resistant *Staphylococcus aureus* (MRSA) and *Burkholderia cepacia*. In this study, it was reported that each of MMA and SMA had superior anti-bacterial activity against the test bacteria, while MA showed anti-bacterial effect against MRSA only.

Even though macrolactin compounds are known to have various pharmacological activities, studies about the anti-inflammatory effect of macrolactin compounds have never been reported until now.

Inflammation is a defensive response to an injury which has occurred in an affected part of a living system. That is, an inflammatory response is a defensive response for restoring the original condition by responding to a harmful stimulus and removing the injury caused by the stimulus.

Nitric oxide (hereinafter, "NO"), one of the substances that induce inflammation, is produced in endothelial cells or macrophages in a normal state. NO, a mediator participating in vasodilation, platelet adhesion and aggregation, neurotransmission, movement of the digestive system, and erection, etc., is produced in inflammatory cells and non-immune cells, and also performs a defensive action against microorganism infection. Stimulation due to lipopolysaccharide (hereinafter, "LPS"), inflammation-inducing factors and irradiation, etc. induces the expression of intracellular iNOS protein and produces NO continuously to induce inflammatory disease.

Another inflammation-inducing substance, prostaglandin E2 (hereinafter, "PGE2") is a kind of hormone derived from arachidonic acid and participates in various physiological activities. PGE2 is produced by the expression of COX-2 protein. Drugs that suppress the expression of COX-2 have analgesic, antiedemic, antipyretic, anti-inflammatory and anticoagulant effects, etc. by the inhibition of PGE2 production in inflammatory foci, and therefore they can be used for prevention and treatment of thrombus, edema, infarction, stroke and cerebrovascular diseases.

The above two inflammation-inducing substances, iNOS and COX-2, are closely related to each other. For example, excessively produced NO may affect the expression of COX-2. Accordingly, an inhibitor of the activity of iNOS and COX-2 is considered to have high potential for development as a drug for preventing and treating various diseases (e.g., inflammatory diseases) caused by excessive production of NO and PGE2 metabolites.

Until now, steroids and non-steroidal anti-inflammatory drugs (NSAIDs) have been used appropriately for the treatment of acute and chronic inflammatory diseases. However, conventional anti-inflammatory agents have considerable adverse effects, especially when used over a long time. Thus, it is highly required to develop a novel inflammatory agent with few side effects.

DISCLOSURE

Technical Problem

Considering the above problem of conventional anti-inflammatory agents, the object of the present invention is to provide an anti-inflammatory use of macrolactin compounds such as MA, MMA and SMA, which are produced from *Bacillus polyfermenticus* KJS-2 (KCCM10769P). Especially, the present invention provides a use of the macrolactin compounds having a superior anti-inflammatory activity which is due to inhibiting the formation of iNOS and COX-2.

In addition, the object of the present invention is to provide a pharmaceutical composition comprising the above macrolactin compounds as active ingredients for preventing and treating inflammatory diseases.

Technical Solution

In one aspect, the present invention provides an anti-inflammatory use of MA of Formula (1), MMA of Formula (2)

and SMA of Formula (3) which are produced from the *Bacillus polyfermenticus* KJS-2 (KCCM10769P) strain.

In another aspect, the present invention provides an anti-inflammatory use of the above macrolactins such as MA, MMA and SMA for inhibiting the formation of iNOS and COX-2 proteins and pro-inflammatory cytokines.

In still another aspect, the present invention provides a pharmaceutical composition comprising the above macrolactin compounds for preventing and treating inflammatory diseases.

[Formula 1]

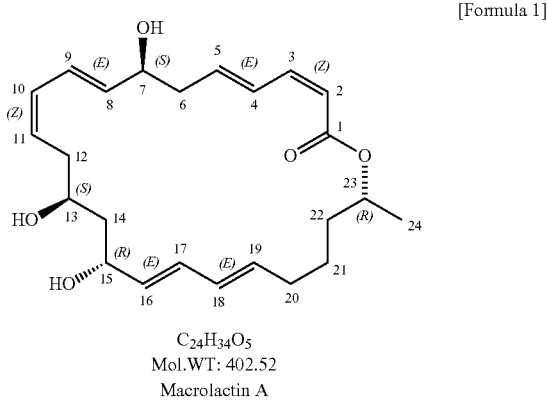

C₂₄H₃₄O₅
Mol.WT: 402.52
Macrolactin A

[Formula 2]

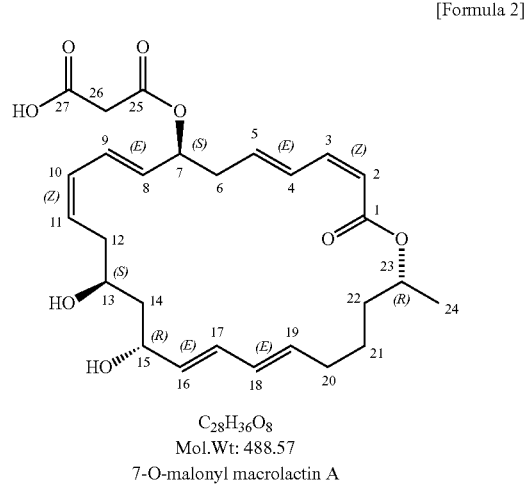

C₂₈H₃₆O₈
Mol.Wt: 488.57
7-O-malonyl macrolactin A

[Formula 3]

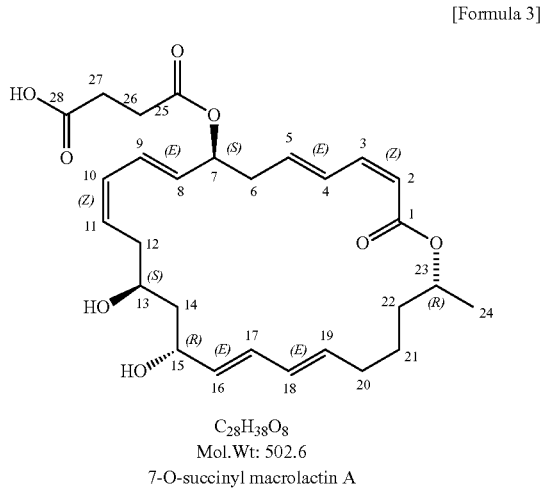

C₂₈H₃₈O₈
Mol.Wt: 502.6
7-O-succinyl macrolactin A

The present invention is explained in more detail hereinafter.

In order to obtain MA of Formula (1) and MMA of Formula (2), *Bacillus polyfermenticus* KJS-2 (KCCM10769P) which is separated by the present inventors is fermented in an MA medium. The fermented broth is extracted by ethyl acetate, and the extract is concentrated. The subject product is separated and purified according to the procedures of Example 1.

In order to obtain SMA of Formula (3), the above strain is fermented in tryptic soy broth (TSB) containing HP-20 resin. The subject product is separated and purified according to the procedures of Example 1.

Structures of the purified products are analyzed by LC/Mass and nuclear magnetic resonance (NMR).

Until now, no research has been reported about the anti-inflammatory effect of the above macrolactin compounds, MA, MMA and SMA.

The present inventors have confirmed the anti-inflammatory effects of the above macrolactin compounds to accomplish the present invention. In order to investigate the anti-inflammatory effects, a murine macrophage RAW264.7 cell line treated with each of the purified compounds was stimulated by LPS (0.1 μg/mL or 1.0 μg/mL, Sigma), and then the formation of inflammation-inducing substances 1) NO and 2) PEG2 and the expression of enzymes related to their formation were analyzed. The formation of 3) pro-inflammatory cytokines, TNF-α, IL-1β, IL-6 and GM-CSF were also analyzed by the same procedures.

1) Suppression of NO formation was determined by Griess reaction. As a result, it was confirmed that MA, MMA and SMA all strongly inhibited the formation of NO, compared to the control group treated with LPS only. The inhibition effect on NO formation of the macrolactin compounds was especially comparable to or superior to that of hydrocortisone.

NO formation is related to iNOS protein. Once iNOS activity is induced, a large amount of NO is formed for a long time. NO is known for its adverse effect on a living system such as pathological vasodilation, cytotoxicity, tissue damage, etc., and is also known to accelerate such inflammatory responses as vascular permeability and edema, and aggravate inflammation by promoting biosynthesis of inflammatory mediators under inflammation conditions.

In order to investigate the mechanism of action for suppressing NO formation, a murine macrophage RAW264.7 treated with each of the macrolactin compounds was stimulated by LPS to induce the formation of iNOS, and then the extent of suppression of iNOS formation in each compound was determined by real-time PCR and western blot.

As a result, MA, MMA and SMA all strongly suppressed the expression of iNOS mRNA in the gene expression by real-time PCR, and the suppression effects were comparable to or superior to that of hydrocortisone. In the protein expression level determined by western blot, the present macrolactin compounds also showed strong suppression effects compared to the control group treated with LPS only.

Through the above results, the present macrolactin compounds are considered to suppress NO formation by the action of suppressing the expression of iNOS protein.

2) Suppression of another inflammatory mediator PGE2 was determined by using an enzyme-linked immunosorbent assay (ELISA) kit. As a result, it was confirmed that MA, MMA and SMA all strongly inhibited the formation of PGE2, compared to the control group treated with LPS only. Especially, the inhibition effect of PGE2 formation of the macrolactin compounds was comparable to or superior to that of hydrocortisone. Many anti-inflammatory drugs have a mechanism of action to suppress PGE2 synthesis, which is due to the inhibition of formation and activity of COX-2 protein. PGE2 synthesized by COX-2 mediates inflammatory response. It is known that PGE2 produced by COX-2 protein stimulates inflammatory response, immune response, and vasculogenesis, and is involved in the onset of cancer. In order to investigate the linkage between the suppression of PGE2 synthesis and the suppression of COX-2 protein synthesis, a murine macrophage RAW264.7 treated with each of the macrolactin compounds was stimulated by LPS to induce the formation of COX-2, and then the extent of suppression of COX-2 protein formation in each compound was determined by real-time PCR and western blot. As a result, the macrolactin compounds of the present invention strongly suppressed the expression of COX-2 mRNA, and the suppression activities were comparable to or superior to that of hydrocortisone. In the expression of COX-2 protein determined by western blot, the present macrolactin compounds also showed strong suppression effects compared to that of the control group treated with LPS only.

According to the above results, the present macrolactin compounds are considered to strongly inhibit PGE2 formation by suppressing the expression of COX-2 protein.

Through the above results, it was confirmed that the present macrolactin compounds strongly inhibited the formation of NO and PGE2 by the action of suppressing the formation of iNOS and COX-2 protein.

3) Suppression of pro-inflammatory cytokines by the present macrolactin compounds was determined by using a mouse ELISA kit (KOMA Biotech).

As a result of TNF-α determination, it was confirmed that MA, MMA and SMA all inhibited the formation of TNF-α, compared to the control group treated with LPS only. In addition, the inhibition effect on TNF-α formation of the macrolactin compounds was comparable to or superior to that of hydrocortisone. MA has an especially superior inhibition effect on TNF-α formation compared to other control substances.

As a result of IL-1β determination, it was confirmed that each of MA and SMA strongly inhibited the formation of IL-1β, and the inhibition effect on IL-1β formation of the macrolactin compounds was comparable to or superior to that of hydrocortisone.

As a result of IL-6 determination, it was confirmed that MA, MMA and SMA all strongly inhibited the formation of IL-6. The inhibition effects on IL-1β formation of the macrolactin compounds were not superior to that of hydrocortisone.

As a result of GM-CSF determination, it was confirmed that each of MA and SMA strongly inhibited the formation of GM-CSF. The inhibition effects on GM-CSF formation of the macrolactin compounds were superior to that of hydrocortisone.

According to the above results, the present macrolactin compounds are considered to strongly inhibit pro-inflammatory cytokines which are involved in both acute and chronic inflammation.

In addition, the cytotoxicities on a murine macrophage RAW264.7 of the present macrolactin compounds and hydrocortisone which has been typically used as anti-inflammatory agent was determined by thiazolyl blue tetrazolium bromide (hereinafter, "MTT") analysis. As a result, the cytotoxicities of the present macrolactin compounds were lower than that of hydrocortisone.

BEST MODE

The present invention is explained in more detail by the following examples. However, these examples seek to illustrate the present invention only, and the scope of the present invention is not limited by them.

Example 1

Production of Macrolactin A, 7-O-Malonyl Macrolactin A, and 7-O-Succinyl Macrolactin A from *Bacillus polyfermenticus* KJS-2 Strain, Separation and Analysis of Structure Thereof Step 1: Production of Macrolactin A and 7-O-Malonyl Macrolactin A from the *Bacillus polyfermenticus* KJS-2 Strain, and Separation Thereof A fermentation process using the *Bacillus polyfermenticus* KJS-2 (KCCM10769P) strain isolated by the present inventors was carried out in MA medium to obtain MA and MMA. The composition of the MA medium was as follows:

Nutrient broth (Difco) 16 g/L, skim milk 10 g/L, 2.5 µM FeSO4, 500 µM, CaCl$_2$, 1 mM MgSO$_4$, 13 mM KCl.

The fermentation process was carried out under the condition of 0.143 vvm of air inflow and 200 rpm at 30° C., and the pH 6.8 was maintained by 1N HCl and 3N NaOH. The fermented broth was extracted by ethyl acetate and then concentrated. The concentrate was dissolved by methanol to make a sample for middle pressure liquid chromatography (hereinafter, "MPLC"). Buchi MPLC system (Buchi pump C-605, column 1.5×23 cm, Fraction collector Buchi C-660) was used and LiChroprep C-18 (40-63 µm, Merck) was filled in the column. The detection was made at 262 nm, and the mobile phase was 40% acetonitrile with a flow rate of 15 mL/min. After the fermented broth extract was injected into the MPLC column, the fractions corresponding to number 1 and 2 peaks of FIG. 1 were concentrated to make samples for succeeding analysis.

Step 2: Production of 7-O-Succinyl Macrolactin A from the Bacillus polyfermenticus KJS-2 Strain, and Separation Thereof The Bacillus polyfermenticus KJS-2 (KCCM10769P) strain isolated by the present inventors was inoculated in tryptic soy broth (TSB) medium containing 10% of HP-20 resin (Mitsubishi Chemical) and cultured at 200 rpm and 30° C. for 2.5 days. After the culture, HP-20 resin was collected and then washed with water. Methanol was used to elute the combined substance. The methanol elute was concentrated to make a sample for MPLC. The operation condition of MPLC was the same as described above. The fraction corresponding to the indicated peak of FIG. 2 was concentrated to make a sample for succeeding analysis.

Step 3: Condition of Analysis and Structure Elucidation

Figure 3:
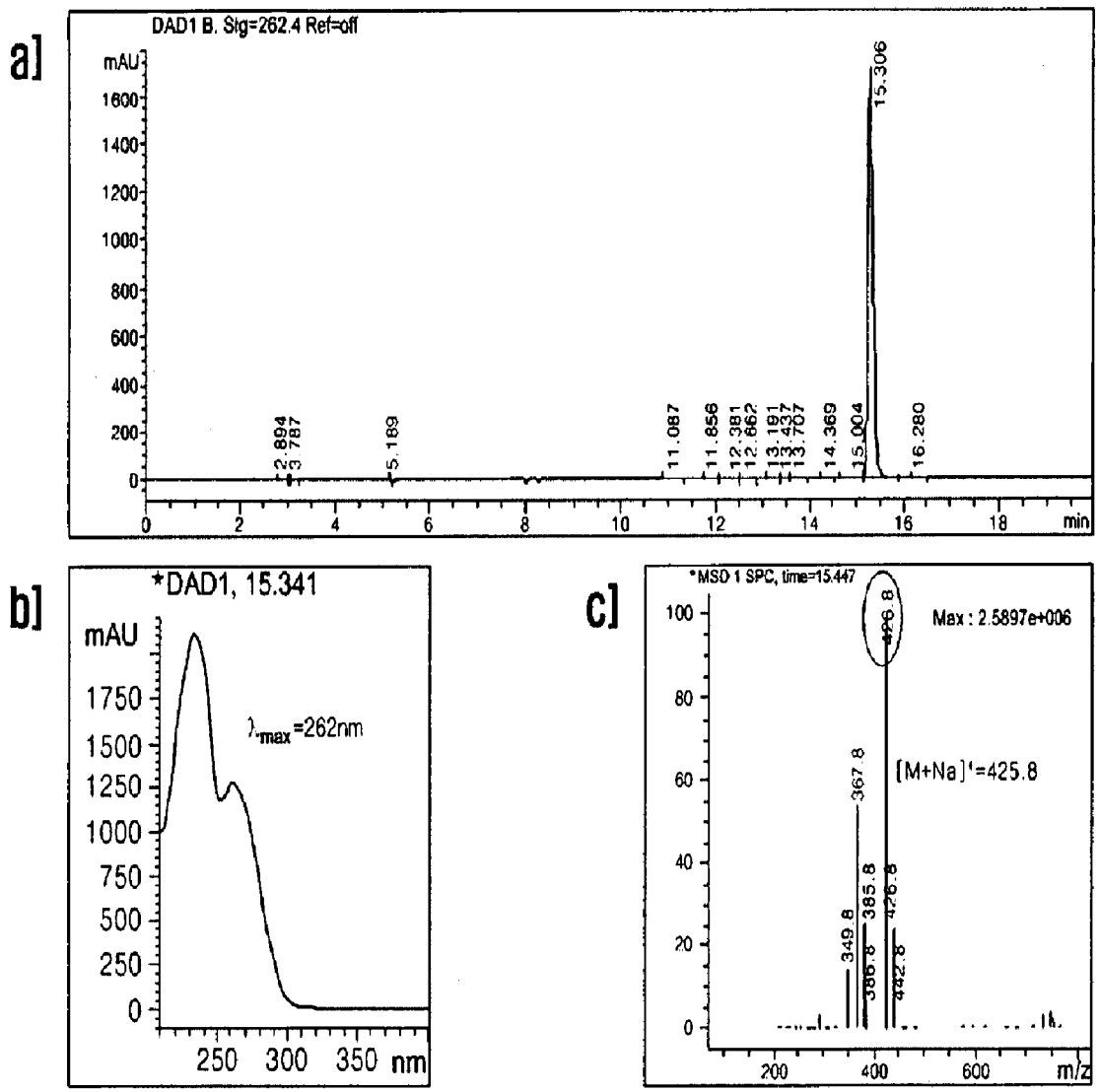
FIG. 3 is a result of LC/Mass analysis of macrolactin A produced by the *Bacillus polyfermenticus* KJS-2 strain: a) LC chromatogram determined at 262 nm; b) UV spectrum; and c) electrospray ionize-spectrum (ESI-spectrum).
Figure 4:
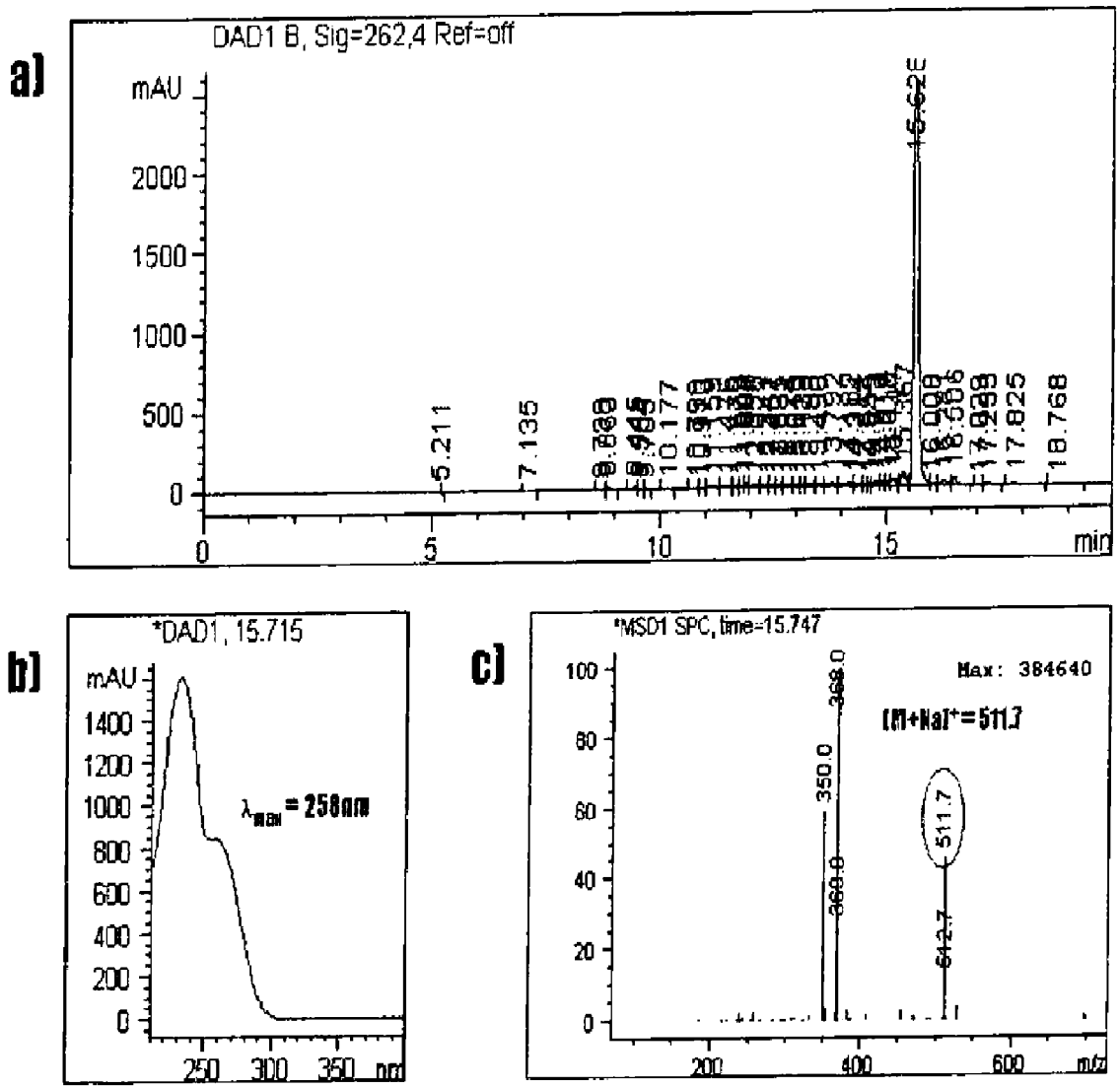
FIG. 4 is a result of LC/Mass analysis of 7-O-malonyl macrolactin A produced by the *Bacillus polyfermenticus* KJS-2 strain: a) LC chromatogram determined at 262 nm; b) UV spectrum; and c) electrospray ionize-spectrum (ESI-spectrum).
Figure 5:
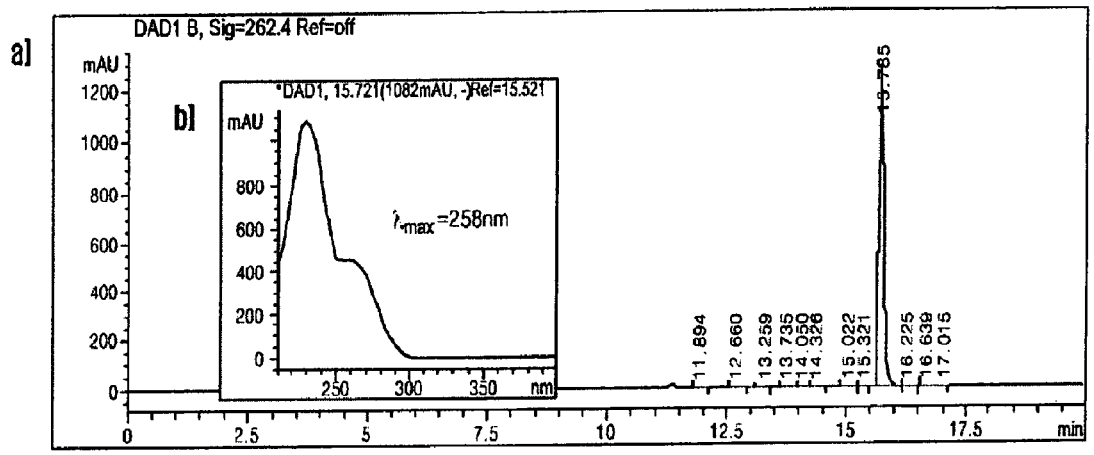
FIG. 5 is a result of LC/Mass analysis of 7-O-succinyl macrolactin A produced by the *Bacillus polyfermenticus* KJS-2 strain: a) LC chromatogram determined at 262 nm; b) UV spectrum; and c) electrospray ionize-spectrum (ESI-spectrum).

Each substance purified in Steps 1 and 2 was analyzed by the following equipment and conditions. Mass analysis was carried out by agilent 1,100 series LC/Mass equipped with Zorbax SB-C18 column (particle size 5 µm, 4.6×250 mm). The mobile phase of LC was acetonitrile and water containing 0.1% formic acid, and the LC analysis condition used a gradient solvent of 0 to 100% acetonitrile for 20 minutes at 1 mL/min of flow rate and detected at 262 nm. Mass analysis condition was AP-ESI (atmosphere pressure-electro spray ionization) mode using 13 L/min of drying gas flow, 50 psi of vapor pressure and 350° C. of drying gas temperature. The capillary voltage was 4,000 V at cation mode and 3,500 V at anion mode, the mass range was 100 m/z to 1,000 m/z, and the fragment voltage was 150 V. Each substance purified in Steps 1 and 2 was analyzed under the above conditions, and FIGS. 3 to 5 show the results. The results of mass analysis of each compound were as follows.

Figure 1:
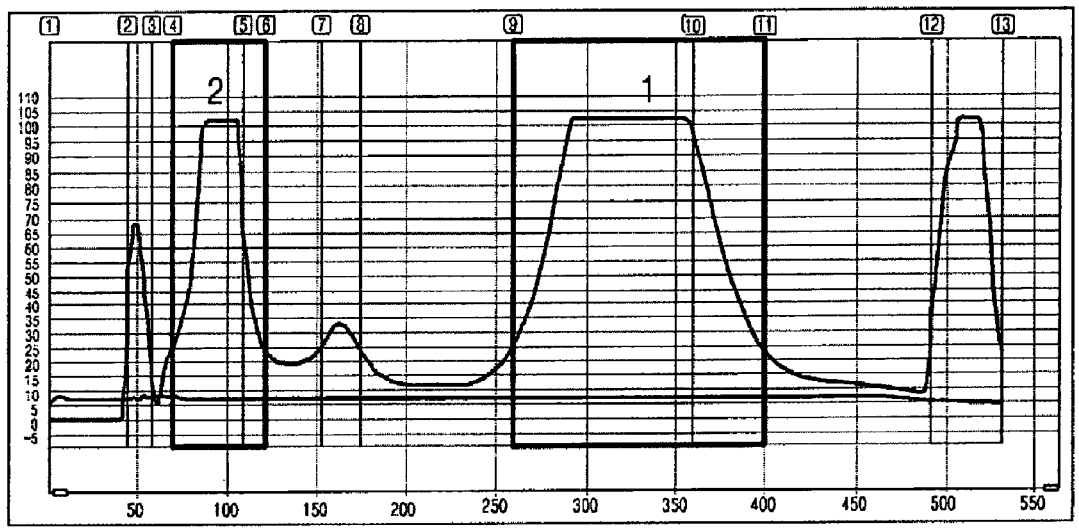
FIG. 1 is an MPLC chromatogram of the fermented broth extract of the *Bacillus polyfermenticus* KJS-2 strain.

In FIG. 1, the fraction of No. 1 was identified as [M+Na]$^+$ 425.4 m/z, [M+K]$^+$ 441.4 m/z, maximum absorbance ($\lambda_{max}$) 262 nm, and purity 98.3%, and the fraction of No. 2, as [M+Na]$^+$ 511.7 m/z, maximum absorbance ($\lambda_{max}$) 258 nm, and purity 84.88%. The fraction of FIG. 2 was identified as [M+Na]$^+$ 526.0 m/z, [M-H]$^-$ 502.0 m/z, maximum absorbance ($\lambda_{max}$) 258 nm and purity 97.02%.

About 30 mg of each purified substance was dissolved in DMSO-d6 solution and then analyzed by MNR to identify the chemical structure thereof. For the identification, various NMR techniques such as $^1$H-NMR, $^{13}$C-NMR, DEPT-90, DEPT-135, Homo COZY, HMQC, and HMBC were used, and a proton decoupling method was also used to solve the problem of $^1$H-NMR spectrum.

As a result of NMR analysis, No. 1 fraction of FIG. 1 and FIG. 3 was identified as MA, the results of which are shown in Tables 1 and 4. Specific rotation of the substance determined by polarimeter (POLAX-D, Atago) was −10 at 17° C. (c=4.0, methanol), which confirmed the substance to be MA, the same compound as Formula 1.

TABLE 1

Result of NMR analysis of macrolactin A produced from the Bacillus polyfermenticus KJS-2 strain

| No. | $\delta_H$ (500 MHz) m | J [Hz] | $\delta_C$ (125 MHz) | | HMBC |
|---|---|---|---|---|---|
| 1 | — | — | 165.8870 | C | — |
| 2 | 5.55 d | 11.68 | 117.0377 | CH | C 1, 4 |
| 3 | 6.65 dd | 11.54, 11.51 | 143.8163 | CH | C 1, 4, 5 |
| 4 | 7.06 dd | 11.56, 15.13 | 128.4909 | CH | C 3, 6 |
| 5 | 6.19 dt | 15.17, 14.68 | 142.7268 | CH | C 3, 4, 6, 7 |
| 6 | 2.32 m | — | 42.2335 | CH$_2$ | C 4, 5, 7, 8 |
| 7 | 4.16 m | — | 70.0227 | CH | C 5, 6, 8, 9 |
| 8 | 5.71 dd | 5.23, 15.16 | 137.8565 | CH | C 6, 7, 10, 11 |
| 9 | 6.48 dd | 15.06, 11.21 | 124.0051 | CH | C 7, 8, 10, 11 |
| 10 | 6.02 dd | 10.9, 10.85 | 121.9103 | CH | C 8, 9, 12 |
| 11 | 5.49 m | — | 128.1563 | CH | C 9, 12 |
| 12a | 2.36 m | — | 35.8599 | CH$_2$ | C 10, 11, 13 |
| 12b | 2.14 m | — | | | C 10, 11, 13, 14 |
| 13 | 3.64 m | — | 67.1403 | CH | C 11, 15 |
| 14 | 1.42 m | — | 43.8152 | CH$_2$ | C 15, 16 |
| 15 | 4.14 m | — | 67.5901 | CH | C 13, 14, 16, 17 |
| 16 | 5.49 dd | 6.15, 14.85 | 136.4129 | CH | C 14, 15, 17, 18, 19 |
| 17 | 6.04 dd | 14.84, 10.35 | 128.6258 | CH | C 18, 19 |
| 18 | 5.96 dd | 10.5, 14.62 | 130.6756 | CH | C 16, 17 |
| 19 | 5.59 dt | 14.36, 14.18 | 133.4564 | CH | C 17, 20, 21 |
| 20 | 2.07 m | — | 31.8226 | CH$_2$ | C 18, 19, 21, 22 |
| 21 | 1.44 m | — | 24.4871 | CH$_2$ | C 19 |
| 22 | 1.52 m | — | 34.7418 | CH$_2$ | C 21, 23 |
| 23 | 4.9 m | — | 70.5721 | CH | C 1, 21 |
| 24 | 1.2 d | 6.27 | 19.9672 | CH$_3$ | C 22, 23 |

As a result of NMR analysis, No. 2 fraction of FIG. 1 and FIG. 4 was identified as MMA, the results of which are shown in Tables 2 and 4. Specific rotation of the substance determined by polarimeter (POLAX-D, Atago) was −5 at 17° C. (c=4.0, methanol), which confirmed the substance to be MMA, the same compound as Formula 2.

TABLE 2

Result of NMR analysis of 7-O-malonyl macrolactin A produced from the Bacillus polyfermenticus KJS-2 strain

| No. | $\delta_H$ (500 MHz) m | J [Hz] | $\delta_C$ (125 MHz) | | HMBC |
|---|---|---|---|---|---|
| 1 | — | — | 165.75 | C | — |
| 2 | 5.58 d | 11.38 | 117.88 | CH | C 1, 3, 4 |
| 3 | 6.62 dd | 11.34, 11.92 | 143.3 | CH | C 1, 4, 5 |
| 4 | 7.1 dd | 11.74, 15.65 | 129.35 | CH | C 2, 3, 6 |
| 5 | 6.1 dt | 15.23, 14.62 | 139.72 | CH | C 3, 6, 7 |
| 6 | 2.54 m | — | 38.74 | CH$_2$ | C 4, 5, 7 |
| 7 | 5.39 m | — | 73.64 | CH | C 5, 6, 8, 9, 25 |
| 8 | 5.72 dd | 5.68, 15.41 | 131.03 | CH | C 6, 7, 10 |
| 9 | 6.53 dd | 15.26, 11.08 | 126.93 | CH | C 7, 11 |
| 10 | 6.04 dd | 11.33, 10.53 | 129.26 | CH | C 8, 9, 11, 12 |
| 11 | 5.59 m | — | 130.26 | CH | C 9, 10, 12 |
| 12a | 2.4 m | — | 35.8 | CH$_2$ | C 11, 13, 14 |
| 12b | 2.17 m | — | | | |
| 13 | 3.67 m | — | 67.07 | CH | C 11, 14, 15 |
| 14 | 1.4 M | — | 43.81 | CH$_2$ | C 12, 15, 16 |
| 15 | 4.16 m | — | 67.53 | CH | C 13, 14, 16, 17 |
| 16 | 5.52 dd | 6.04, 14.62 | 136.48 | CH | C 14, 15, 18 |
| 17 | 6.03 m | — | 128.62 | CH | C 15, 18, 19 |
| 18 | 6.0 dd | 10.58, 14.52 | 130.67 | CH | C 16, 17, 20 |
| 19 | 5.57 m | — | 133.31 | CH | C 17, 18, 20, 21 |
| 20 | 2.07 m | — | 31.74 | CH$_2$ | C 18, 19, 21, 22 |
| 21a | 1.54 m | — | 24.49 | CH$_2$ | C 19, 20, 22, 23 |
| 21b | 1.41 m | — | | | |

TABLE 2-continued

Result of NMR analysis of 7-O-malonyl macrolactin A produced from the *Bacillus polyfermenticus* KJS-2 strain

| No. | $\delta_H$ (500 MHz) m | J [Hz] | $\delta_C$ (125 MHz) | | HMBC |
|---|---|---|---|---|---|
| 22a | 1.56 m | — | 34.72 | $CH_2$ | C 20, 21, 23, 24 |
| 22b | 1.42 m | — | | | |
| 23 | 4.93 m | — | 70.61 | CH | C 1, 21, 22, 24 |
| 24 | 1.2 d | 6.27 | 19.96 | $CH_3$ | C 21, 22, 23 |
| 25 | — — | — | 166.47 | C | |
| 26 | 3.39 s | — | 42.02 | $CH_2$ | C 7, 25, 27 |
| 27 | — — | — | 168.27 | C | — |

Figure 2:
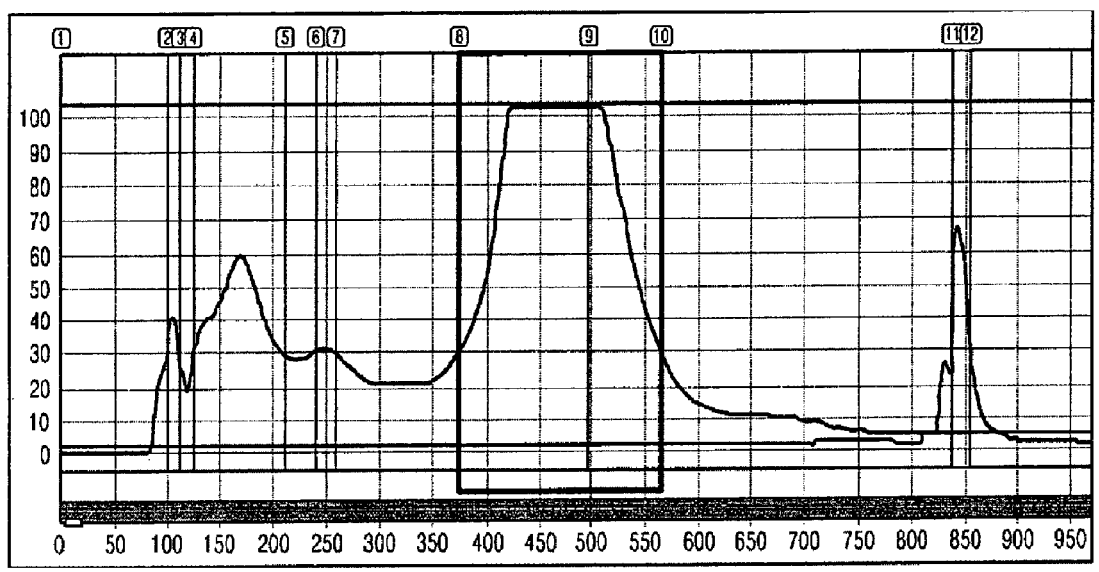
FIG. 2 is an MPLC chromatogram of the culture extract of the *Bacillus polyfermenticus* KJS-2 strain.

As a result of NMR analysis, the fraction of FIG. 2 and FIG. 4 was identified as SMA, the results of which are shown in Tables 3 and 4. Specific rotation of the substance determined by polarimeter (POLAX-D, Atago) was −15 at 17° C. (c=4.0, methanol), which confirmed the substance to be MMA, the same compound as Formula 3.

TABLE 3

Result of NMR analysis of 7-O-succinyl macrolactin A produced from the *Bacillus polyfermenticus* KJS-2 strain

| No. | $\delta_H$ (500 MHz) m | J [Hz] | $\delta_C$ (125 MHz) | | HMBC |
|---|---|---|---|---|---|
| 1 | — — | — | 165.2841 | C | — |
| 2 | 5.56 d | 11.47 | 117.3471 | CH | C 1, 3, 4, 23 |
| 3 | 6.63 dd | 11.48, 11.51 | 142.8233 | CH | C 1, 4, 5 |
| 4 | 7.09 dd | 11.63, 15.1 | 128.8817 | CH | C 2, 3, 6 |
| 5 | 6.08 dt | 15.15, 14.71 | 139.5009 | CH | C 3, 6, 7 |
| 6 | 2.56 m | — | 38.3741 | $CH_2$ | C 4, 5, 7, 8 |
| 7 | 5.38 m | — | 72.2324 | CH | C 5, 6, 8, 9, 25 |
| 8 | 5.71 dd | 5.48, 15.24 | 130.9608 | CH | C 6, 7, 9, 10 |
| 9 | 6.47 dd | 15.15, 11.17 | 126.0905 | CH | C 7, 8, 10, 11 |
| 10 | 6.052 dd | 11.08, 10.5 | 128.7842 | CH | C, 8, 9, 11, 12 |
| 11 | 5.59 m | — | 129.6256 | CH | C 9, 10, 12, 13 |
| 12a | 2.41 m | — | 35.2705 | $CH_2$ | C 10, 11, 13, 14 |
| 12b | 2.17 m | — | | | C 10, 11, 13, 14 |
| 13 | 3.64 m | — | 66.6737 | CH | C 11, 14, 15 |
| 14 | 1.42 m | — | 43.5422 | $CH_2$ | C 12, 13, 15, 16 |
| 15 | 4.15 m | — | 67.1329 | CH | C 13, 14, 16, 17 |
| 16 | 5.52 dd | 6.12, 14.52 | 135.9759 | CH | C 14, 15, 18 |
| 17 | 6.055 dd | 14.12, 10.63 | 128.1934 | CH | C 15, 16, 18, 19 |
| 18 | 6.0 dd | 10.59, 14.99 | 130.1854 | CH | C 16, 17, 20 |
| 19 | 5.59 dt | 14.52, 13.85 | 132.8811 | CH | C 17, 20, 21 |
| 20 | 2.07 m | — | 31.3294 | $CH_2$ | C 18, 19, 21, 22 |
| 21 | 1.45 m | — | 24.0792 | $CH_2$ | C 19, 20, 22, 23 |
| 22 | 1.54 m | — | 34.2894 | $CH_2$ | C 20, 21, 23, 24 |
| 23 | 4.94 m | — | 70.1668 | CH | C 1, 21, 22, 24 |
| 24 | 1.2 d | 6.27 | 19.4997 | $CH_3$ | C 22, 23 |
| 25 | — — | — | 171.3042 | C | — |

TABLE 3-continued

Result of NMR analysis of 7-O-succinyl macrolactin A produced from the *Bacillus polyfermenticus* KJS-2 strain

| No. | $\delta_H$ (500 MHz) m | J [Hz] | $\delta_C$ (125 MHz) | | HMBC |
|---|---|---|---|---|---|
| 26 | 2.47 — | — | 28.6109 | $CH_2$ | C 7, 25, 27, 28 |
| 27 | 2.50 — | — | 28.7757 | $CH_2$ | C 25, 26, 28 |
| 28 | — — | — | 173.1817 | C | — |

Table 4 shows the production methods, yields, purities and properties of MA, MMA and SMA produced from the *Bacillus polyfermenticus* KJS-2 strain investigated by the present invention.

TABLE 4

Production methods, yields, purities and properties of MA, MMA and SMA produced from the *Bacillus polyfermenticus* KJS-2 strain

| Compound | Media | Culture method | Culture period days | Yield mg/L | Purity % | Molecular formula | Molecular weight | $\lambda_{initial}$ | $[\alpha]^{17}_D$ (c in MeOH) | ESI-MS m/z |
|---|---|---|---|---|---|---|---|---|---|---|
| MA | MA medium | Fermentation | 2 | 58 | 98.3 | $C_{24}H_{35}O_5$ | 402.52 | 230.262 | −10 (4.0) | 425.4 $[M + Na]^+$ 441.4 $[M + K]^+$ |
| MMA | MA medium | Fermentation | 0.5 | 16 | 84.9 | $C_{27}H_{36}O_8$ | 488.57 | 230.258 | −5 (4.0) | 511.7 $[M + Na]^+$ 487.7 $[M − H]^−$ |
| SMA | TSB | Flask incubation | 2.5 | 138 | 97.02 | $C_{28}H_{36}O_8$ | 502.6 | 230.258 | −15 (4.0) | 525.6 $[M + Na]^−$ 501.6 $[M − H]^−$ |

MA, macrolactin A; MMA, 7-O-malonyl macrolactin A; SMA, 7-O-succinyl macrolactin A Example 2

Investigation of Anti-Inflammatory Activities of the Macrolactin Compounds on a Murine Macrophage RAW264.7 Cell Line RAW264.7, a murine macrophage cell line, was obtained from Korean Cell Line Bank (KCLB). It was cultured in Dulvecco's modified Eagle's medium (DMEM, LONZA) containing 10% fetal bovine serum (FBS, LONZA) and 1% penicillin/streptomycin (Sigma) in an incubator at 37° C. under 5% $CO_2$ and then sub-cultured when the cell density reached 80%. After RAW264.7 cells were cultured for 24 hours, MA (1-100 μM), MMA (10 μM), SMA (10 μM) and hydrocortisone (10 μM), which is a well-known substance having anti-inflammatory activity, were added. One hour after the addition, LPS (0.1 or 1.0 μg/ml, Sigma) was added to the mixture, which was then cultured for 8 or 16 hours. Dimethyl sulfoxide (hereinafter, "DMSO") was used as a negative control, while LPS (0.1 or 1.0 μg/ml, Sigma) was used as a positive control without adding the macrolactin compounds.

Experiment 1: Inhibition Effect on NO Formation

NO concentration in cell culture was determined by using a Nitrate/Nitrite colorimetric assay Kit (Cayman). Murine macrophage RAW264.7 cells adjusted to $1 \times 10^5$ cells/well were cultured in a 6-well plate for 24 hours under the conditions mentioned in Example 2, and then further cultured for 16 hours after being treated with the present macrolactin compounds and LPS (0.1 μg/ml, Sigma). The cultured media were treated with Griess reagent R1 (sulfanilamide) and then Griess reagent R2 (N-(1-Naphthyl)-ethylenediamine) in a 96-well plate provided by the manufacturer, and then detected the formation of purple azo group from nitrite. The amount of produced NO was calculated using the calibration curve which had been made through the standard solution provided by the manufacturer at an absorbance of 540 nm in a UV spectrometer.

Figure 6:
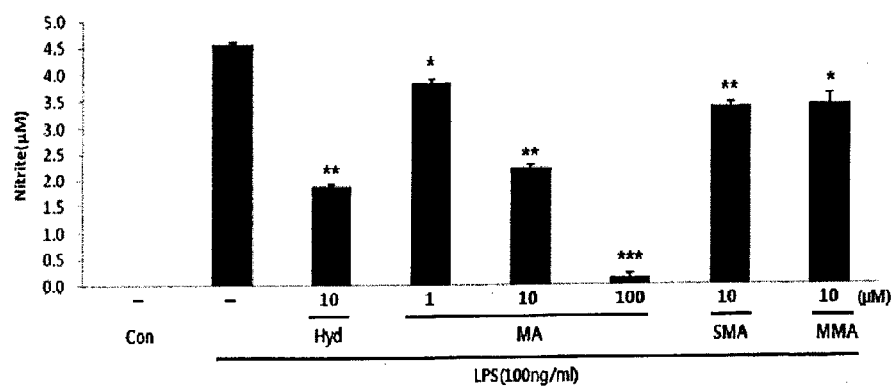
FIG. 6 is a graph showing the inhibition effect on NO formation in RAW264.7 cells according to the present macrolactin compounds.

As a result, both MA and hydrocortisone strongly inhibited NO formation, while MMA and SMA showed low inhibition activities (see FIG. 6).

Experiment 2: Inhibition Effect on PGE2 Formation

The amount of formed PGE2, an intracellular anti-inflammatory factor, was determined by using an Amersham prostaglandin E2 biotrak Enzymeimmunoassay (EIA) system Kit (GE Healthcare). Murine macrophage RAW264.7 cells adjusted to $2 \times 10^4$ cells/well were cultured in a 96-well plate for 24 hours under the conditions mentioned in Example 2 and then further cultured for 16 hours after being treated with the present macrolactin compounds and LPS (0.1 μg/ml, Sigma). The amount of produced PGE2 was calculated using the calibration curve which had been made through the standard solution provided by the manufacturer at an absorbance of 450 nm in a UV spectrometer. The $r^2$ value of the calibration curve against the standard substance was above 0.99.

Figure 7:
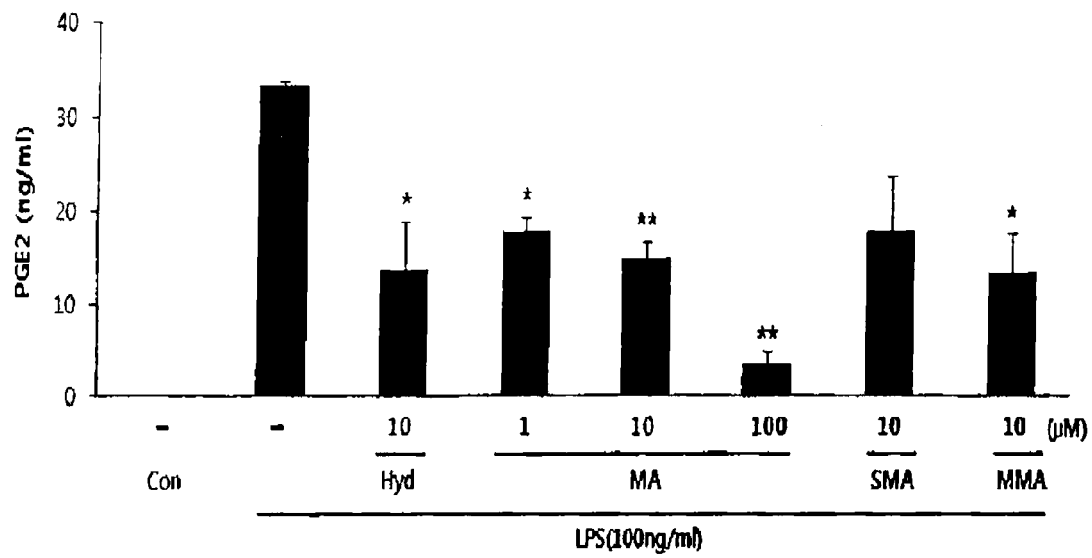
FIG. 7 is a graph showing the inhibition effect on PGE2 formation in RAW264.7 cells according to the present macrolactin compounds.

As a result, MA, MMA and SMA all strongly inhibited PGE2 formation, and the inhibition activities were similar to or comparable to that of hydrocortisone (see FIG. 7).

Experiment 3: Effect on the Expression of iNOS and COX-2 mRNA

The effect of the present macrolactin compounds on the expression of intracellular inflammatory factors, iNOS and COX-2 mRNA was investigated. Murine macrophage RAW264.7 cells adjusted to $1 \times 10^5$ cells/well were cultured in a 6-well plate for 24 hours under the conditions mentioned in Example 2 and then further cultured for 16 hours after being treated with the present macrolactin compounds and LPS (0.1 μg/ml, Sigma). Total RNA of the cultured cells was isolated by Trizol reagent (Sigma) under RNase-free conditions. A cDNA synthesis kit (TAKARA) was used to obtain a template for PCR using the separated total RNA. To the mixture of 1 μl of Oligo dT Primer (50 μM), 1 μl of dNTP Mixture (10 mM each) and 2 μg of the template RNA, RNase-free dH$_2$O was added to adjust the total volume to 10 μl. The mixture was maintained at 65° C. for 5 minutes and then in ice for 2 minutes. To the mixture of 10 μl of the mixture, 4 μl of 5× PrimeScript™ buffer, 0.5 μl of RNase inhibitor (40 U/μl), and 0.5 μl of PrimeScript™ RTase (200 U/μl), RNase-free dH$_2$O was added to adjust the total volume to 20 μl. The mixture was reacted at 42° C. for 30 minutes to synthesize cDNA.

To the mixture of 25-50 ng of the synthesized cDNA, 5 μl of sensiMixPlus SYBR 2× buffer (Quantance) and 0.25 pmol of each primer as shown in Table 5, distilled water was added to adjust the total volume to 10 μl. The extent of iNOS and COX-2 mRNA expression of the mixture was determined by using a real-time gene amplifier (Corbett Life Science Rotorgene 6000). The operating condition of the real-time gene amplifier was as follows: initial denaturation started at 95° C. for 5 minutes and was then repeated 50 times at 94° C. for 30 seconds, at 57° C. for 30 seconds and 72° C. for 30 seconds. When the mRNA expressions of the samples were compared with each other, that of the housekeeping gene was determined at the same time and then the relative quantity was calculated. By compensating the amount of RNA for the measured value of the housekeeping gene, the amount of mRNA produced in each sample was calculated to Ct (Threshold cycle) value.

Figure 8:
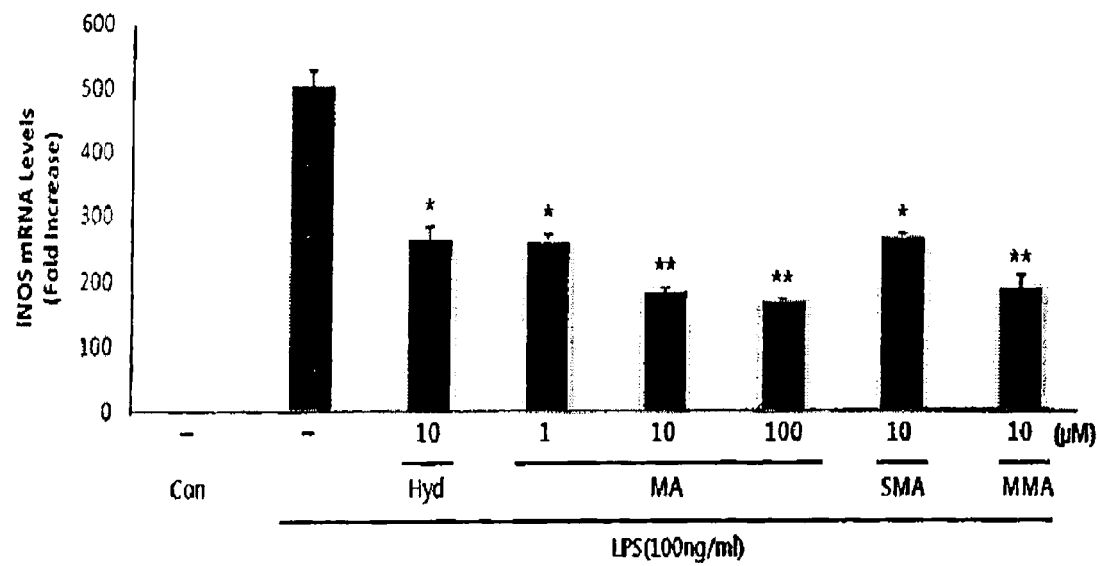
FIG. 8 is a graph showing the inhibition effect on iNOS mRNA expression in RAW264.7 cells according to the present macrolactin compounds.
Figure 9:
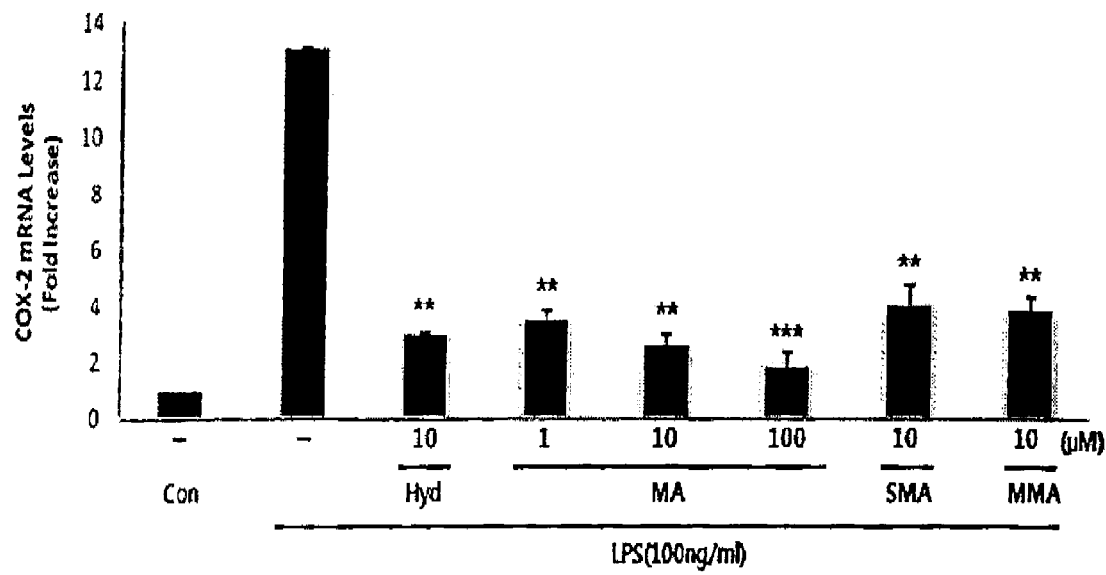
FIG. 9 is a graph showing the inhibition effect on COX-2 mRNA expression in RAW264.7 cells according to the present macrolactin compounds.

As a result, MA, MMA and SMA all strongly inhibited the expressions of iNOS and COX-2 mRNA, and the inhibition activities were similar to or comparable to that of hydrocortisone (see FIGS. 8 and 9).

TABLE 5

Nucleoside sequences and fragment sizes of the primers used in real-time gene amplification

| Gene | Primer sequences | Fragment size (bp) |
|------|------------------|--------------------|
| COX-2 | F 5'-CAGCAAATCCTTGCTGTTCC-3'<br>R 5'-TGGGCAAAGAATGCAAACAT-3' | 450 |
| iNOS | F 5'-ATGTCCGAAGCAAACATCACA-3'<br>R 5'-TAATGTCCAGGAAGTAGGTGAGG-3' | 450 |
| GAPDH | F 5'-GGCATTGCTCTCAATGACAA-3'<br>R 5'-TGTGAGGGAGATGCTCAGTG-3' | 200 |

Experiment 4: Effect on the Formation of iNOS and COX-2 Protein

The effect of the present macrolactin compounds on the formation of intracellular inflammatory factor, iNOS and COX-2 protein was investigated. Murine macrophage RAW264.7 cells adjusted to $1 \times 10^6$ cells/dish were cultured in a 100 mm dish for 24 hours under the conditions mentioned in Example 2 and then further cultured for 16 hours after being treated with the present macrolactin compounds and LPS (0.1 μg/ml, Sigma). The cells were washed 2-3 times with cold PBS and then collected. 100 μl of 50 mM Tris-HCl buffer, pH7.5 (0.1 M KCl, 1 mM EDTA, 1 mM DTT, 0.2 mM PMSF) were added to the collected cells, which were lysed by using liquid nitrogen. The lysate was centrifuged at 4° C. for 10 minutes at 13,000 rpm to collect the supernatant. Protein was quantitatively analyzed by the Bradford method. 50 μg of the protein was subjected to sodium dodecyl sulfate-polyacrylamide gel electrophoresis (SDS-PAGE). The SDS-PAGE gel was transferred to nitrocellulose membrane (Amersham) at 50 V for 2 hours. The nitrocellulose membrane was washed twice with 1× Tris buffered saline (TBS; 0.1 M NaCl, 10 mM Tris-HCl), to which was added 3% gelatin solution for blocking non-specific protein reaction and then reacted at room temperature for 1 hour. After 3% gelatin solution was removed, 1× Tris buffered saline-Tween (TBS-T; 0.1M NaCl, 10 mM Tris-HCl, 0.1% Tween 20) was added thereto. To investigate the expression of iNOS and COX-2 protein, anti-mouse iNOS (Cell Signaling), anti-mouse COX-2 (Cell Signaling) and anti-mouse GAPDH (Cell Signaling) were diluted with 1×TBS-T in the ratio of 1:1,000 and reacted at room temperature for 1 hour. The reactant was washed twice with 1×TBS-T and then reacted with anti-rabbit IgG (Sigma) bound with secondary antibody alkaline phosphatase and diluted with 1×TBS-T in the ratio of 1:5,000 for 1 hour. The reactant was washed three times with 1×TBS-T, and the protein band corresponding to the antibody was identified by using BCIP/NBT Color Development Substrate (5-bromo-4-chloro-3-indolyl-phosphate/nitro blue tetrazolium, Promega).

Figure 10:
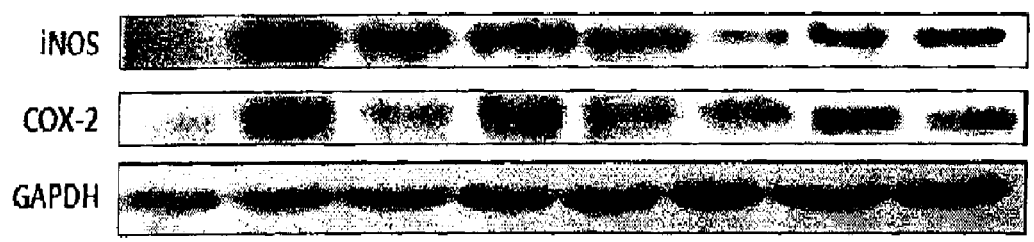
FIG. 10 is a result showing the inhibition effect on iNOS and COX-2 protein production in RAW264.7 cells according to the present macrolactin compounds.

As a result, MA, MMA and SMA all strongly inhibited the formation of iNOS and COX-2 protein, and the inhibition activities were similar to or comparable to that of hydrocortisone (see FIG. 10).

Experiment 5: Effect on Cytotoxicity

MTT analysis was used to investigate the cytotoxic effects on murine macrophage RAW264.7 of the present macrolactin compounds. The cells adjusted to $4\times10^4$ cells/well were cultured in a 96-well plate for 24 hours under the conditions mentioned in Example 2 and then further cultured for 16 hours after being treated with the present macrolactin compounds. After the medium was removed, 100 μl of MTT solution (2 mg/ml PBS) was added, and then the mixture was cultured in an incubator at 37° C. under 5% $CO_2$ for 4 hours. After the MTT solution was removed, 100 μl of DMSO was added, and then the mixture was shake-cultured for 30 minutes in the dark. After the culture, the amount of free formazan was determined at 540 nm by using an ELISA reader.

Figure 11:
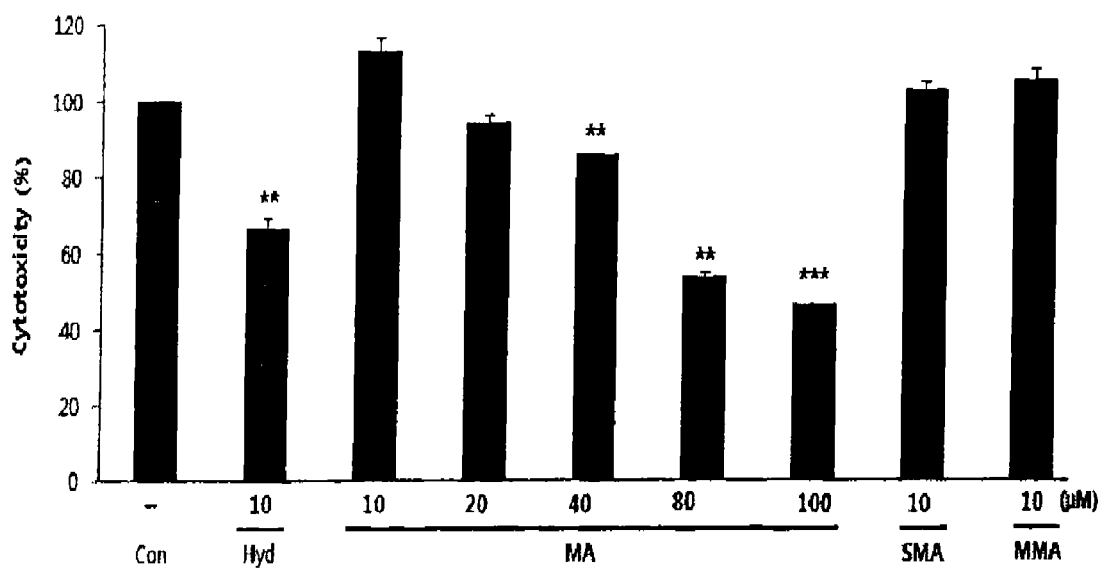
FIG. 11 is a graph showing the cytotoxicity on RAW264.7 cells according to the present macrolactin compounds.
Figure 12:
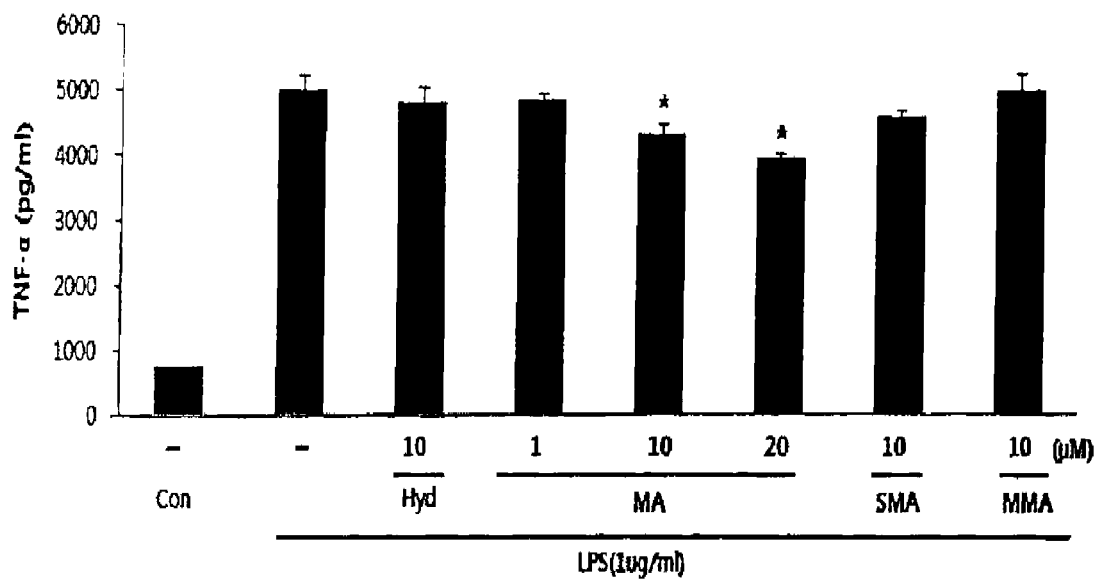
FIG. 12 is a graph showing the inhibition effect on TNF-α formation in RAW264.7 cells according to the present macrolactin compounds.
Figure 13:
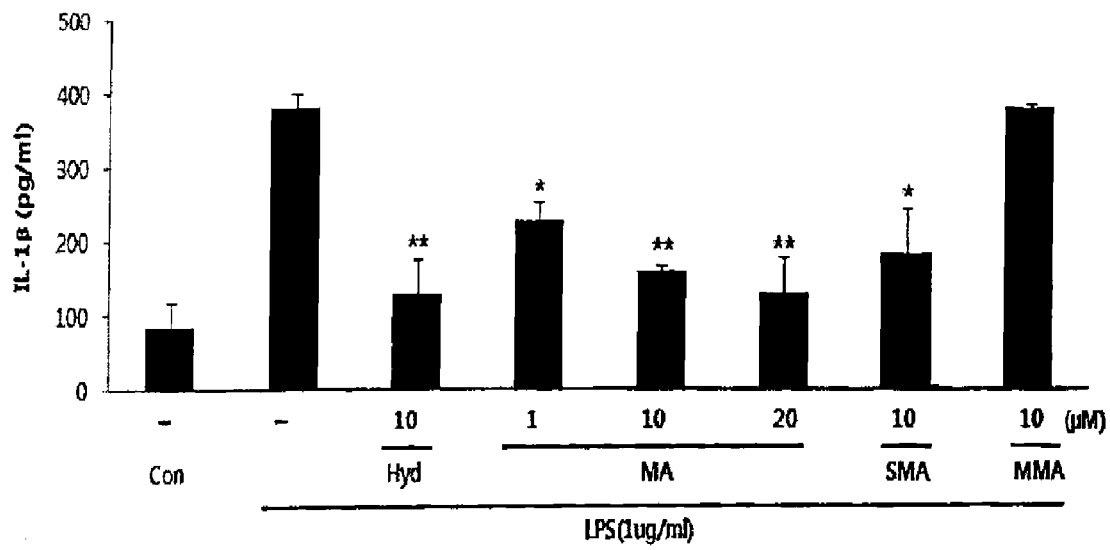
FIG. 13 is a graph showing the inhibition effect on IL-1β formation in RAW264.7 cells according to the present macrolactin compounds.
Figure 14:
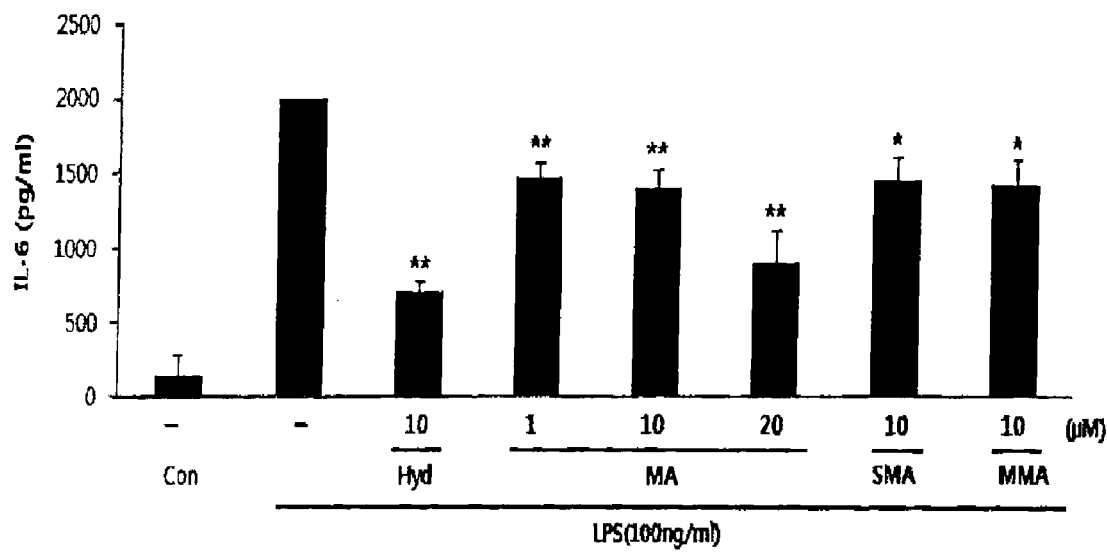
FIG. 14 is a graph showing the inhibition effect on IL-6 formation in RAW264.7 cells according to the present macrolactin compounds.
Figure 15:
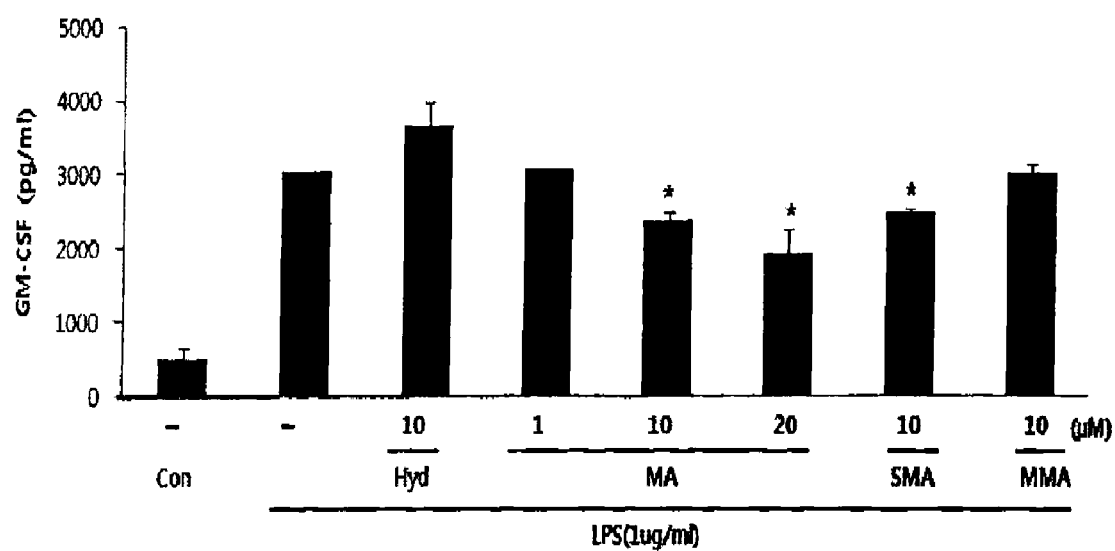
FIG. 15 is a graph showing the inhibition effect on GM-CSF formation in RAW264.7 cells according to the present macrolactin compounds.

As a result, it was confirmed that MA, MMA and SMA all had lower cytotoxicities compared to that of hydrocortisone (see FIG. 11).

INDUSTRIAL APPLICABILITY

The present invention provides macrolactin compounds, MA, MMA and SMA, which are produced from the *Bacillus polyfermenticus* KJS-2 (KCCM10769P) strain. The macrolactin compounds directly suppress the expression and formation of inducible nitric oxide synthetase (iNOS) and cyclooxygenase-2 (COX-2) which are proteins related to the formation of inflammatory mediators, and inhibit the formation of its metabolites, NO and PGE2, so that they may be used to prevent and treat various diseases (e.g., inflammatory diseases) caused by excessive production of the metabolites. Furthermore, the macrolactin compounds have low cytotoxicities compared to those of conventional anti-inflammatory agents. Accordingly, the present macrolactin compounds are expected to solve the problem of adverse effects caused by conventional anti-inflammatory agents.

We claim:

1. A method of inhibiting formation of a mediator selected from the group consisting of nitric oxide (NO), prostaglandin E2 (PGE2), tumor necrosis factor-alpha (TNF-α), interleukin-1β (IL-1β), interleukin-6 (IL-6) and granulocyte macrophage colony-stimulating factor (GM-CSF), or inhibiting activity of inducible nitric oxide synthetase (iNOS) and cyclooxygenase-2 (COX-2) in a subject comprising:
    administering an effective amount of a composition comprising an active agent selected from the group consisting of macrolactin A, 7-O-malonyl macrolactin A, and 7-O-succinyl macrolactin A to a subject in need thereof,
    whereby the formation of a mediator selected from the group consisting of nitric oxide (NO), prostaglandin E2 (PGE2), tumor necrosis factor-alpha (TNF-α), interleukin-1β (IL-1β), interleukin-6 (IL-6) and granulocyte macrophage colony-stimulating factor (GM-CSF), or the activity of iNOS and COX-2 in the subject is inhibited,
    wherein the subject does not have bacterial infection.

2. The method of claim 1, wherein the active agent is macrolactin A which is produced from the *Bacillus polyfermenticus* KJS-2 (KCCM10769P) strain.

3. The method of claim 1, wherein the active agent is 7-O-malonyl macrolactin A which is produced from the *Bacillus* polyfermenticus KJS-2 (KCCM10769P) strain.

4. The method of claim 1, wherein the active agent is 7-O-succinyl macrolactin A which is produced from the *Bacillus polyfermenticus* KJS-2 (KCCM10769P) strain.

\* \* \* \* \*